(12) United States Patent
OuYang et al.

(10) Patent No.: US 11,771,304 B1
(45) Date of Patent: Oct. 3, 2023

(54) MINIMALLY INVASIVE ENDOSCOPE

(71) Applicant: MicronVision Corp., Bellevue, WA (US)

(72) Inventors: Xiaolong OuYang, Bellevue, WA (US); Shih-Ping Wang, Los Altos, CA (US)

(73) Assignee: MicronVision Corp., Bellevue, WA (US)

( * ) Notice: Subject to any disclaimer, the term of this patent is extended or adjusted under 35 U.S.C. 154(b) by 0 days.

(21) Appl. No.: 17/720,143

(22) Filed: Apr. 13, 2022

Related U.S. Application Data

(63) Continuation-in-part of application No. 17/521,397, filed on Nov. 8, 2021.
(Continued)

(51) Int. Cl.
*A61B 1/00* (2006.01)
*A61B 1/05* (2006.01)
(Continued)

(52) U.S. Cl.
CPC ...... *A61B 1/00032* (2013.01); *A61B 1/00131* (2013.01); *A61B 1/015* (2013.01); *A61B 1/018* (2013.01); *A61B 1/05* (2013.01)

(58) Field of Classification Search
CPC . A61B 1/012; A61B 1/00032; A61B 1/00034; A61B 1/00066; A61B 1/00071;
(Continued)

(56) References Cited

U.S. PATENT DOCUMENTS

| 4,854,302 A | 8/1989 | Allred, III |
| 4,979,497 A | 12/1990 | Matsura |

(Continued)

FOREIGN PATENT DOCUMENTS

| CN | 102858275 | 1/2013 |
| EP | 1690512 | 8/2006 |

(Continued)

OTHER PUBLICATIONS

International Search Report and Written Opinion of PCT/US2016/18670, dated Jul. 12, 2016.
(Continued)

*Primary Examiner* — Ryan N Henderson
(74) *Attorney, Agent, or Firm* — Wissing Miller LLP

(57) ABSTRACT

An endoscope in which a reusable portion is inserted nearly all the way into a hollow, pistol-grip handle of a single-use portion and the protruding part of the reusable portion and an adjacent part of the handle are covered with a flexible and resilient cap. The same cap covers the open end of the handle when the single-use portion is shipped from a manufacturing site. At a user's facility, a health professional tears the pouch, removes the cap from the handle, inserts the reusable portion, and covers the distal end of the reusable portion and an adjacent part of the handle with the same cap. Typically, a remote display connects to the endoscope wirelessly or through a cable, with a connector that fits through a hole in the cap configured to keep fluids from entering around the connector. The wireless transmission preferably uses a proprietary protocol to preserve medical data confidentiality.

13 Claims, 15 Drawing Sheets

Related U.S. Application Data

(60) Provisional application No. 63/176,307, filed on Apr. 18, 2021, provisional application No. 63/138,528, filed on Jan. 18, 2021, provisional application No. 63/128,105, filed on Dec. 20, 2020, provisional application No. 63/122,739, filed on Dec. 8, 2020, provisional application No. 63/118,617, filed on Nov. 25, 2020, provisional application No. 63/113,960, filed on Nov. 15, 2020, provisional application No. 63/295,913, filed on Jan. 2, 2022, provisional application No. 63/299,829, filed on Jan. 14, 2022, provisional application No. 63/302,563, filed on Jan. 25, 2022, provisional application No. 63/303,690, filed on Jan. 27, 2022, provisional application No. 63/310,336, filed on Feb. 15, 2022, provisional application No. 63/299,960, filed on Jan. 15, 2022.

(51) Int. Cl.
 *A61B 1/018* (2006.01)
 *A61B 1/015* (2006.01)

(58) Field of Classification Search
 CPC ... A61B 1/00103; A61B 1/00105; A61B 1/05; A61B 1/00142; A61B 1/00144
 See application file for complete search history.

(56) References Cited

U.S. PATENT DOCUMENTS

| | | | |
|---|---|---|---|
| 5,010,876 A | 4/1991 | Henley | |
| 5,188,093 A | 2/1993 | Lafferty | |
| 5,281,214 A | 1/1994 | Wilkins | |
| 5,323,767 A | 6/1994 | Lafferty | |
| 5,329,936 A | 7/1994 | Lafferty | |
| 5,486,155 A | 1/1996 | Muller | |
| 5,549,547 A | 8/1996 | Cohen | |
| 5,569,163 A | 10/1996 | Francis | |
| 5,632,717 A * | 5/1997 | Yoon | A61B 17/320016 600/129 |
| 5,666,561 A | 9/1997 | Stephenson | |
| 5,667,472 A | 9/1997 | Finn | |
| 5,667,476 A | 9/1997 | Frassica et al. | |
| 5,785,644 A | 7/1998 | Grabover | |
| 5,860,953 A | 1/1999 | Snoke | |
| 5,873,814 A | 2/1999 | Adair | |
| 5,928,137 A | 7/1999 | Green | |
| 5,935,141 A | 8/1999 | Weldon | |
| 5,957,947 A | 9/1999 | Wattiez | |
| 6,004,264 A * | 12/1999 | Sano | G02B 23/2469 600/199 |
| 6,007,531 A | 12/1999 | Snoke | |
| 6,007,546 A | 12/1999 | Snow | |
| 6,017,322 A | 1/2000 | Snoke | |
| 6,033,378 A | 3/2000 | Lundquist | |
| 6,059,719 A | 5/2000 | Yamamato et al. | |
| 6,095,970 A | 8/2000 | Hidaka | |
| 6,165,123 A * | 12/2000 | Thompson | A61B 1/00078 600/152 |
| 6,174,307 B1 | 1/2001 | Daniel | |
| 6,210,416 B1 | 4/2001 | Chu | |
| 6,211,904 B1 | 4/2001 | Adair | |
| 6,221,007 B1 | 4/2001 | Green | |
| 6,221,070 B1 | 4/2001 | Tu et al. | |
| 6,261,226 B1 | 7/2001 | McKenna | |
| 6,280,386 B1 | 8/2001 | Alfano | |
| 6,331,174 B1 | 12/2001 | Reinhard | |
| 6,387,043 B1 | 5/2002 | Yoon | |
| 6,398,743 B1 | 6/2002 | Halseth | |
| 6,507,699 B2 | 1/2003 | Lemoine | |
| 6,518,823 B1 | 2/2003 | Kawai | |
| 6,793,882 B1 | 9/2004 | Verschuur | |
| 6,917,380 B1 | 7/2005 | Tay | |
| 7,256,446 B2 | 8/2007 | Hu | |
| 7,428,378 B1 | 9/2008 | Warpakowski | |
| 7,507,205 B2 | 3/2009 | Borovsky | |
| 7,591,799 B2 | 9/2009 | Selkee | |
| 7,606,609 B2 | 10/2009 | Muranushi | |
| 7,780,650 B2 | 8/2010 | Frassica | |
| 7,798,995 B2 | 9/2010 | Yue | |
| 7,931,616 B2 | 4/2011 | Selkee | |
| 7,946,981 B1 | 5/2011 | Cubb | |
| 8,057,464 B2 | 9/2011 | Chen | |
| 8,052,609 B2 | 11/2011 | Harhen | |
| 8,187,171 B2 | 5/2012 | Irion | |
| 8,197,398 B2 | 6/2012 | Scholly | |
| 8,235,975 B2 | 8/2012 | Chen | |
| 8,361,775 B2 | 4/2013 | Flower | |
| 8,460,182 B2 | 6/2013 | Ouyang | |
| 8,523,808 B2 | 9/2013 | Selkee | |
| 8,696,552 B2 | 4/2014 | Whitman | |
| 8,803,960 B2 | 8/2014 | Sonnenschein | |
| 8,834,357 B2 | 9/2014 | Oskin | |
| 8,845,522 B2 | 9/2014 | McIntyre | |
| 8,952,312 B2 | 2/2015 | Blanqart | |
| 8,998,844 B2 | 4/2015 | Reed | |
| 9,473,749 B2 * | 10/2016 | Selby | H04N 7/183 |
| 9,649,014 B2 | 5/2017 | Ouyang | |
| 9,736,342 B2 | 8/2017 | Mueckl | |
| 9,895,048 B2 * | 2/2018 | Ouyang | A61B 1/00034 |
| 10,278,563 B2 | 5/2019 | Ouyang | |
| 10,292,571 B2 | 5/2019 | Ouyang | |
| 10,595,710 B2 | 3/2020 | Gill | |
| 2001/0007051 A1 | 7/2001 | Nakashima | |
| 2001/0049509 A1 | 12/2001 | Sekine | |
| 2003/0016284 A1 | 1/2003 | Squilla | |
| 2003/0023142 A1 | 1/2003 | Grabover | |
| 2003/0078476 A1 | 4/2003 | Hill | |
| 2003/0078502 A1 | 4/2003 | Miyaki et al. | |
| 2003/0151680 A1 | 8/2003 | McDermott | |
| 2003/0199735 A1 | 10/2003 | Dickopp | |
| 2004/0054254 A1 | 3/2004 | Miyake | |
| 2004/0054259 A1 | 3/2004 | Hasegawa | |
| 2004/0138558 A1 | 7/2004 | Dunki-Jacobs | |
| 2004/0162572 A1 | 8/2004 | Sauer | |
| 2005/0010178 A1 | 1/2005 | Katz | |
| 2005/0264687 A1 | 1/2005 | Murayama | |
| 2005/0049459 A1 | 3/2005 | Hern | |
| 2005/0085695 A1 | 4/2005 | Sherner | |
| 2005/0154262 A1 | 7/2005 | Banik | |
| 2005/0159646 A1 | 7/2005 | Nordstrom | |
| 2005/0177027 A1 | 8/2005 | Hirata | |
| 2005/0277874 A1 | 12/2005 | Selkee | |
| 2005/0277875 A1 | 12/2005 | Selkee | |
| 2006/0052710 A1 | 3/2006 | Miura | |
| 2006/0063976 A1 | 3/2006 | Aizenfeld | |
| 2006/0114986 A1 | 6/2006 | Knapp | |
| 2006/0152601 A1 | 7/2006 | Parekh | |
| 2006/0167340 A1 * | 7/2006 | Pease | A61B 1/00052 600/109 |
| 2006/0171693 A1 | 8/2006 | Todd | |
| 2006/0173245 A1 | 8/2006 | Todd | |
| 2006/0184227 A1 | 8/2006 | Rust | |
| 2006/0259124 A1 | 11/2006 | Matsuoka | |
| 2006/0287576 A1 | 12/2006 | Tsuji | |
| 2007/0060789 A1 | 3/2007 | Uchimura | |
| 2007/0081920 A1 | 4/2007 | Murphy | |
| 2007/0117437 A1 * | 5/2007 | Boehnlein | G02B 23/2476 439/210 |
| 2007/0129604 A1 | 6/2007 | Hatcher | |
| 2007/0162095 A1 | 7/2007 | Kimmel | |
| 2007/0167678 A1 | 7/2007 | Moskowitz | |
| 2007/0167868 A1 | 7/2007 | Sauer | |
| 2007/0173693 A1 | 7/2007 | Refael | |
| 2007/0188604 A1 | 8/2007 | Miyamoto | |
| 2007/0197875 A1 | 8/2007 | Osaka | |
| 2007/0210162 A1 | 9/2007 | Keen | |
| 2007/0225556 A1 | 9/2007 | Ortiz | |
| 2007/0238927 A1 | 10/2007 | Ueno | |
| 2007/0249904 A1 | 10/2007 | Amano | |
| 2008/0004642 A1 | 1/2008 | Birk | |
| 2008/0071144 A1 | 3/2008 | Kimmel | |
| 2008/0097550 A1 | 4/2008 | Dicks | |

(56) References Cited

U.S. PATENT DOCUMENTS

| | | |
|---|---|---|
| 2008/0108869 A1 | 5/2008 | Sanders |
| 2008/0195125 A1 | 8/2008 | Orbay |
| 2008/0195128 A1 | 8/2008 | Orbay |
| 2008/0225410 A1 | 9/2008 | Ning |
| 2008/0234547 A1 | 9/2008 | Irion et al. |
| 2008/0255416 A1 | 10/2008 | Gilboa |
| 2008/0262306 A1 | 10/2008 | Kawai |
| 2008/0300456 A1 | 12/2008 | Irion |
| 2009/0027489 A1 | 1/2009 | Takemura |
| 2009/0065565 A1 | 3/2009 | Lemoine |
| 2009/0076321 A1 | 3/2009 | Suyama |
| 2009/0076328 A1 | 3/2009 | Root |
| 2009/0080214 A1 | 3/2009 | Watanabe |
| 2009/0105538 A1 | 4/2009 | Van Dam |
| 2009/0118580 A1 | 5/2009 | Sun |
| 2009/0118641 A1 | 5/2009 | Van Dam |
| 2009/0149713 A1 | 7/2009 | Niida |
| 2009/0225159 A1* | 9/2009 | Schneider .......... G02B 23/2484 348/82 |
| 2009/0227897 A1 | 9/2009 | Wendt |
| 2009/0229842 A1* | 9/2009 | Gray .................. B25F 5/02 173/217 |
| 2009/0240245 A1* | 9/2009 | Deville .............. A61B 18/1445 606/33 |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |
| 2010/0026201 A1 | 10/2010 | Frangioni |
| 2011/0009694 A1 | 1/2011 | Schultz |
| 2011/0034769 A1 | 2/2011 | Adair |
| 2011/0037876 A1 | 2/2011 | Talbert |
| 2011/0554446 | 3/2011 | Schultz |
| 2011/0092775 A1 | 4/2011 | Deshmukh |
| 2011/0105839 A1 | 5/2011 | Hoffman |
| 2011/0112622 A1 | 5/2011 | Phan |
| 2011/0130627 A1 | 6/2011 | McGrail |
| 2011/0211115 A1 | 9/2011 | Tsai |
| 2011/0213206 A1 | 9/2011 | Boutillette |
| 2011/0245602 A1 | 10/2011 | Brannon |
| 2011/0264191 A1 | 10/2011 | Rothstein |
| 2011/0288482 A1 | 11/2011 | Farrell |
| 2011/0313245 A1 | 12/2011 | Scholly |
| 2012/0016191 A1 | 1/2012 | Ito |
| 2012/0040305 A1 | 2/2012 | Karazivan |
| 2012/0041533 A1 | 2/2012 | Bertolino |
| 2012/0053515 A1 | 3/2012 | Crank |
| 2012/0100729 A1 | 4/2012 | Edidin |
| 2012/0165627 A1 | 6/2012 | Yamamoto |
| 2012/0165916 A1 | 6/2012 | Jordan |
| 2012/0178991 A1 | 7/2012 | Clark |
| 2012/0206591 A1* | 8/2012 | Selby .................. H04N 23/531 348/82 |
| 2012/0226103 A1 | 9/2012 | Gunday |
| 2012/0236138 A1 | 9/2012 | Liu |
| 2012/0245242 A1 | 9/2012 | Peiffer |
| 2012/0245418 A1 | 9/2012 | Boulais |
| 2012/0253116 A1 | 10/2012 | Sniffin |
| 2012/0259203 A1 | 10/2012 | Devereux |
| 2012/0286020 A1 | 11/2012 | Smith |
| 2012/0289858 A1 | 11/2012 | Ouyang |
| 2013/0035553 A1 | 2/2013 | Kongstorum |
| 2013/0046142 A1 | 2/2013 | Remijan |
| 2013/0057667 A1 | 5/2013 | McGrath |
| 2013/0150672 A1 | 6/2013 | Fujitani |
| 2013/0172676 A1 | 7/2013 | Levy |
| 2013/0190561 A1 | 7/2013 | Oskin |
| 2013/0225921 A1 | 8/2013 | Liu |
| 2013/0253402 A1 | 9/2013 | Badawi |
| 2013/0289559 A1 | 10/2013 | Reid |
| 2013/0324973 A1 | 12/2013 | Reed |
| 2013/0345514 A1 | 12/2013 | Manion |
| 2014/0022649 A1 | 1/2014 | Echhardt |
| 2014/0107416 A1 | 4/2014 | Bimkrant |
| 2014/0111634 A1* | 4/2014 | Mueckl ............... H04N 5/2252 348/82 |
| 2014/0154399 A1 | 6/2014 | Weikart |
| 2014/0180007 A1* | 6/2014 | Edidin ............... A61B 1/00082 600/122 |
| 2014/0188211 A1 | 7/2014 | Roeder |
| 2014/0213848 A1 | 7/2014 | Moskowitz |
| 2014/0228635 A1 | 8/2014 | Tuliakov |
| 2014/0275763 A1* | 9/2014 | King .................. A61B 1/00105 600/110 |
| 2014/0296866 A1 | 10/2014 | Salman |
| 2014/0323991 A1 | 10/2014 | Tang |
| 2015/0005575 A1 | 1/2015 | Kobayashi |
| 2015/0011830 A1 | 1/2015 | Hunter |
| 2015/0018622 A1 | 1/2015 | Tesar |
| 2015/0018710 A1 | 1/2015 | Furlong |
| 2015/0150441 A1 | 6/2015 | Ouyang |
| 2015/0164313 A1 | 6/2015 | Oyuang |
| 2015/0196197 A1 | 7/2015 | Kienzle |
| 2015/0238251 A1 | 8/2015 | Shikhman |
| 2015/0297311 A1 | 10/2015 | Tesar |
| 2016/0000300 A1* | 1/2016 | Williams ............. A61B 1/0676 600/109 |
| 2016/0007833 A1 | 1/2016 | Huang |
| 2016/0073853 A1 | 3/2016 | Venkatesan et al. |
| 2016/0077008 A1 | 3/2016 | Takasu |
| 2016/0174819 A1 | 6/2016 | Ouyang |
| 2016/0334694 A1 | 11/2016 | Liu |
| 2016/0367119 A1 | 12/2016 | Ouyang |
| 2017/0086651 A1 | 3/2017 | Sato |
| 2017/0181853 A1 | 6/2017 | Rothstein |
| 2017/0188793 A1 | 7/2017 | Ouyang |
| 2017/0188795 A1 | 7/2017 | Ouyang |
| 2017/0215699 A1 | 8/2017 | Ouyang |
| 2017/0295347 A1 | 10/2017 | Schneider |
| 2017/0310858 A1 | 10/2017 | Mueckl |
| 2018/0132700 A1* | 5/2018 | Ouyang ............... A61B 1/0684 |
| 2018/0184892 A1 | 7/2018 | Truckai |
| 2018/0235441 A1 | 8/2018 | Huang |
| 2018/0256009 A1 | 9/2018 | Ouyang |
| 2019/0029497 A1 | 1/2019 | Mirza |
| 2019/0142262 A1 | 5/2019 | Inglis |
| 2019/0216325 A1 | 7/2019 | Ouyang |
| 2019/0223691 A1 | 7/2019 | Takatsuji |
| 2019/0246873 A1 | 8/2019 | Lu |
| 2019/0246884 A1 | 8/2019 | Lu et al. |
| 2019/0282071 A1* | 9/2019 | Ouyang ............... A61B 1/0684 |
| 2019/0282073 A1 | 9/2019 | Truckai |
| 2019/0320879 A1 | 10/2019 | Langell |
| 2019/0374095 A1 | 12/2019 | Lord |
| 2020/0204776 A1 | 6/2020 | Themelis |
| 2020/0214739 A1 | 7/2020 | Shi |
| 2020/0275827 A1 | 9/2020 | Weise |
| 2020/0323555 A1* | 10/2020 | Long .................. A61B 17/3403 |
| 2021/0052383 A1 | 2/2021 | Rothstein |
| 2021/0228806 A1 | 7/2021 | Streeter |
| 2021/0244265 A1* | 8/2021 | Chou .................. H04N 7/183 |
| 2021/0401277 A1 | 12/2021 | Ouyang |

FOREIGN PATENT DOCUMENTS

| | | |
|---|---|---|
| EP | 2560589 | 4/2010 |
| EP | 3384879 | 4/2011 |
| EP | 2749258 | 7/2014 |
| EP | 3078354 | 10/2016 |
| JP | 2009148420 | 7/2009 |
| WO | 2011133792 | 10/2011 |
| WO | 2012060932 | 5/2012 |
| WO | 2014031192 | 2/2014 |
| WO | 2014065901 | 5/2015 |

(56) References Cited

FOREIGN PATENT DOCUMENTS

| | | |
|---|---|---|
| WO | 2016032729 | 3/2016 |
| WO | 2016040131 | 3/2016 |
| WO | 2016137838 | 9/2016 |
| WO | 2018136950 | 7/2018 |
| WO | 2019237003 | 12/2019 |

OTHER PUBLICATIONS

International Search Report and Written Opinion of PCT/US2018/014880, dated Jun. 6, 2018.
International Search Report and Written Opinion of PCT/US2018/065396, dated Feb. 24, 2017.
International Search Report and Written Opinion of PCT/US2021/050095 dated Dec. 17, 2021.
International Search Report and Written Opinion of PCT/US2019/036060 dated Aug. 27, 2019.
International Search Report and Written Opinion of PCT/US2017/053171 dated Dec. 5, 2017.
International Preliminary Report on Patentability of PCT/US2017/053171 completed on Jul. 1, 2019.
European Search Report of European Patent Application No. EP19816177 completed Feb. 2, 2022.
Chinese Office Action for Application No. 202221943644.0, dated Dec. 21, 2022.

\* cited by examiner

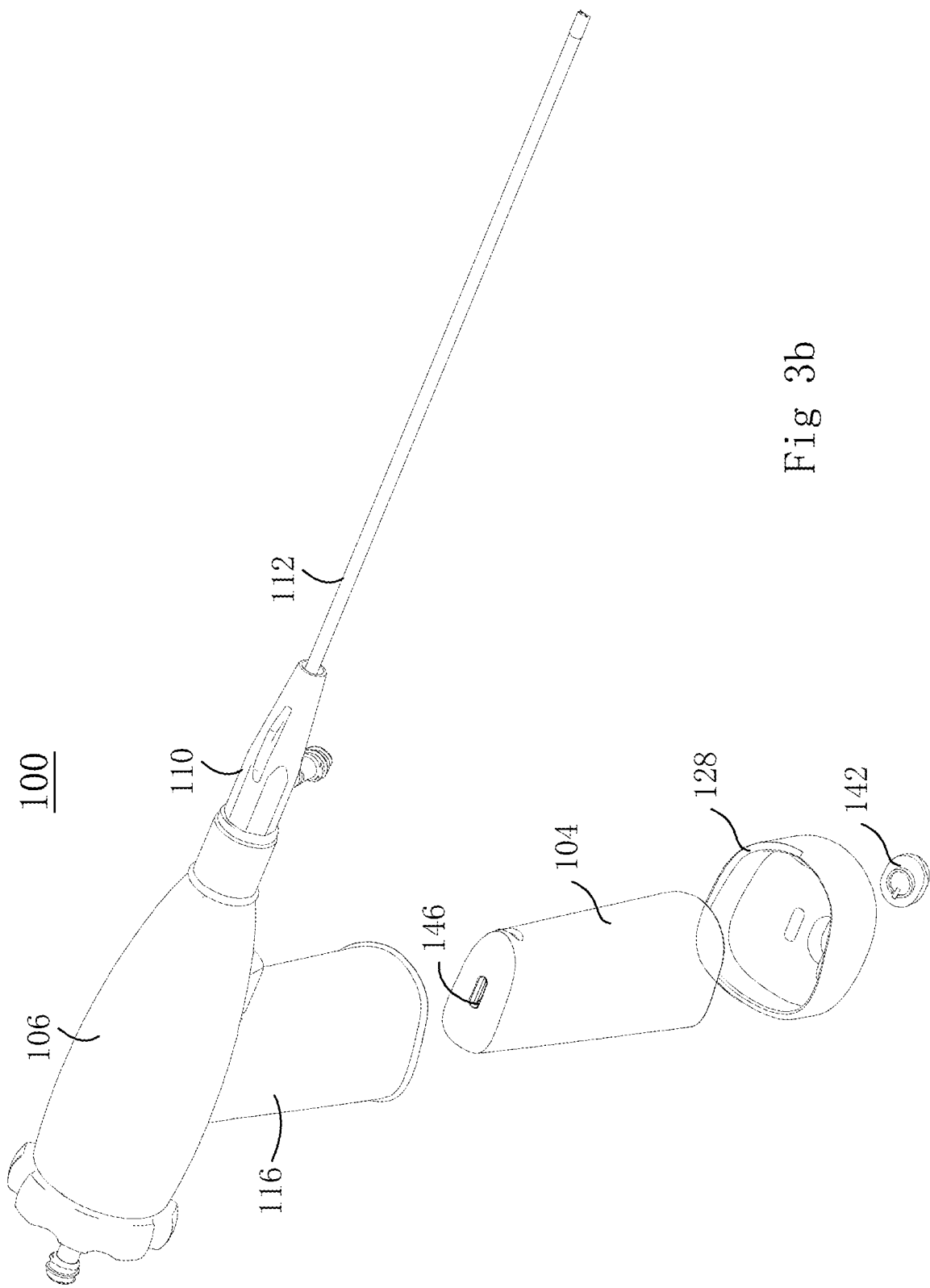

MINIMALLY INVASIVE ENDOSCOPE

REFERENCE TO RELATED APPLICATIONS

This application is a continuation-in-part of parent U.S. patent application Ser. No. 17/521,397 filed Nov. 8, 2021, and claims priority to U.S. Provisional Patent Applications Nos. 63/176,307, filed Apr. 18, 2021; 63/285,061, filed Dec. 1, 2021; 63/295,913, filed Jan. 2, 2022. 63/299,829, filed Jan. 14, 2022; No. 63/302,563, filed Jan. 25, 2022. 63/303, 690, filed Jan. 27, 2022; 63/310,336, filed Feb. 15, 2022; and 63/299,960, filed Jan. 25, 2022. Said parent application in turn claims priority to and incorporates by reference each of the following U.S. Provisional Patent Applications: 63/112, 739 filed Nov. 12, 2020; 63/113,960 filed Nov. 15, 2020; 63/118,617 filed Nov. 25, 2020; 63/128,105 filed Dec. 20, 2020; and 63/138,528 filed Jan. 18, 2021. This application incorporates by reference each of the foregoing patent applications and claims priority thereto.

FIELD

This patent specification relates to endoscopes and more specifically to endoscopes for medical procedures that have lower manufacturing cost and can be fully or partly disposable and avoid or significantly reduce contamination risk.

BACKGROUND

Conventional endoscopy, or direct vision used to examine the interior of a hollow organ or cavity of the body, uses a complex lens system for transmitting the image for the distal tip of the endoscope to a viewer. The lens system is typically an objective lens plus a relay lens system in the case of rigid endoscopes or a bundle of optic fibers in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

Disposable endoscopy is a more recent category of endoscopic instruments. In some cases, the manufacture of endoscopes can be made sufficiently inexpensive to be used on a single patient only. Disposable or single-use endoscopy lessens the risk of cross-contamination and hospital acquired diseases, make it possible to perform procedures in doctors' offices as well as in clinics and hospitals, and reduce the overall cost of medical procedures as they avoid expenses associated with sterilizing and maintaining traditional endoscopes and personnel needed for such maintenance.

Examples of endoscopes, including partly of fully disposable endoscopes, are discussed in the following patents and patent applications, each of which is hereby incorporated by reference: PCT/US 2016/18670 filed Feb. 19, 2016; U.S. Pat. No. 8,702,594, PCT/US2017/053171 filed Sep. 25, 2017; patent application U.S. Ser. No. 16/363,209 filed Sep. 25, 2017 and published as 2019/0216325 A1 on Jul. 18, 2019; PCT/US2019/036060 filed Jun. 7, 2019; patent application U.S. Ser. No. 16/972,989 filed Jun. 7, 2019 and published as 2021/0251789 A1 on Aug. 19, 2021; patent application U.S. Ser. No. 17/362,043 filed Jun. 29, 2021; PCT/US21/50095 filed Sep. 13, 2021; patent application U.S. Ser. No. 17/473,587 filed Sep. 13, 2021; U.S. Pat. No. 8,702,594; PCT/US16/65396 filed Dec. 7, 2016; U.S. Pat. No. 9,649,014; PCT/US2018/014880, filed Jan. 23, 2018; U.S. Pat. Nos. 10,874,287; 9,895,048; 10,524,636; 10,426, 320; 10,278,563; 10,292,571; patent application U.S. Ser. No. 16/407,028 filed May 8, 2019 and published as 20190261836 on Aug. 29, 2019; PCT/US2020/038349 filed Jun. 18, 2020; PCT/US2020/046018 filed Aug. 12, 2020; U.S. Pat. Nos. 10,869,592; 11,013,396; 11,071,442; U.S. patent application Ser. No. 17/122,282 filed Dec. 15, 2020 and published as 20210093169 on Apr. 1, 2021; patent application U.S. Ser. No. 17/145,466 filed Jan. 11, 2021 and published as 20210137352 on May 13, 2021; patent application U.S. Ser. No. 17/349,674 filed Jun. 16, 2020 and published as 20210307591 on Oct. 7, 2021; and patent application U.S. Ser. No. 17/370,575 filed Jul. 8, 2021.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the accompanying drawings in which:

FIGS. 2, 3a and 3b are exploded perspective views of an endoscope from different viewpoints, according to some embodiments.

SUMMARY OF THE DISCLOSURE

Figure 1:
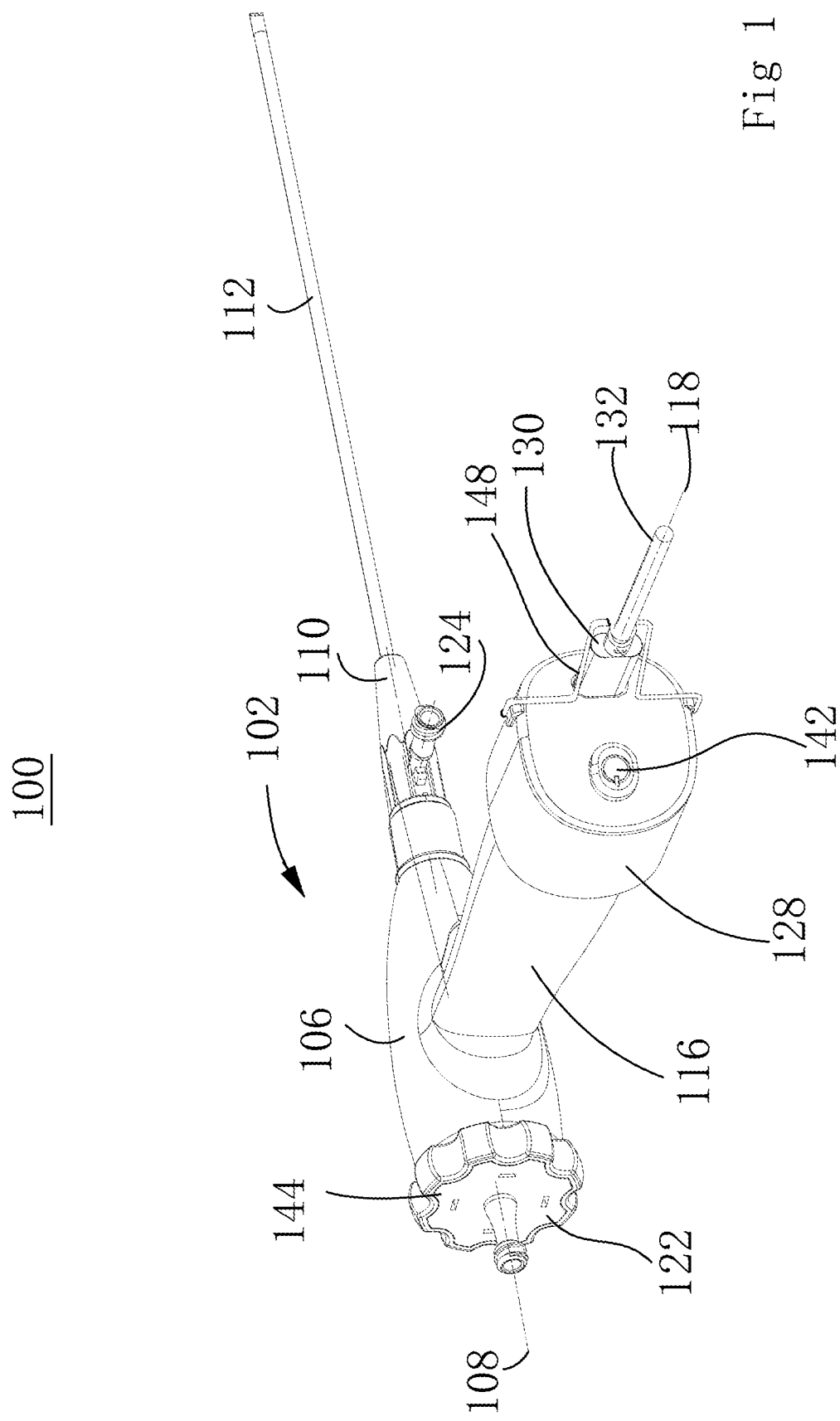
FIG. 1 is perspective view of an assembled endoscope comprising a single-use portion that includes a hollow, funnel-shaped handle open at its bottom end, a reusable portion most of which is received in the hollow handle, and a cap that covers the open end of the handle before the endoscope is assembled but, after the endoscope is assembled, covers a part of the reusable portion that protrudes from the handle and an adjacent part of the handle, according to some embodiments.

According to some embodiments, an endoscope comprises a single-use portion comprising: an elongated housing extending along a cannula axis; a fluid hub extending distally along the cannula axis from the housing; a cannula that extends distally from the fluid hub along the cannula axis and has an imaging module at a distal end; a hollow, funnel-shaped, pistol-grip handle that extends from the housing along a handle axis that is transverse to the cannula axis, has a proximal end that is integral with the housing and an open distal end; an electrical contact inside and at the proximal end of the handle, operatively coupled with said imaging module; a proximal port at a proximal end of the housing, an intermediate port at the fluid hub, and a distal port at a distal end of the cannula; an internal lumen from the proximal port to the distal port, in fluid flow communication with said proximal, intermediate and distal ports. Said fluid hub and cannula are mounted for rotation about the cannula axis relative to the housing. A manual rotation control at the proximal end of the housing is coupled with the fluid hub to rotate the fluid hub and cannula relative to the housing about the cannula axis. The endoscope in this example further includes an elongated reusable portion having a proximal part configured for insertion in the handle along the handle axis and having an electrical contact at a proximal end configured to mate with the electrical contact in the handle when the proximal part of the reusable portion is inserted in the handle; and a cap made of a flexible and resilient material, configured to cover the open distal end of the handle before the reusable portion is inserted in the handle, to be manually removed from the handle prior to insertion of the reusable portion in the handle, and after insertion of the reusable portion in the handle to cover a distal part of the reusable portion that protrudes from the handle along the handle axis as well as an adjacent part of the handle to thereby cover said protruding part of the reusable portion and an interface thereof with the handle.

According to some embodiments, the endoscope can further include one or more of the following features: (a) a sterile pouch enclosing said single use portion, with the cap over and covering the open distal end of the handle, before assembly of the single-use and reusable portions into said endoscope; (b) said reusable portion can includes a battery and control and processing electronics configured to control said imaging module to take images in a field of view and to receive image data from the imaging module, and further includes a facility to convey image data from the endoscope to an external processing/display unit; (c) said facility is configured to convey image data by wireless transmission using a proprietary protocol that is different from conventional WiFi; said facility in the reusable portion is configured to convert received image data into display images and convey display images to an external unit for display; (d) said facility comprises a wireless transmitter/receiver in said reusable portion and further including an external processing/display unit having a wireless transmitter/receiver configured to communicate wirelessly with said transmitter/receiver in the reusable portion and to receive wirelessly and process into display images image data received from the reusable portion, and a display configured to display said display images; (e) said external processing/display unit is configured to automatically search for and connect wirelessly with said reusable portion upon turning ON when the reusable portion is ON and in range; (f) said facility comprises an electrical contact at the distal end of the reusable portion configured to mate with a connector of a cable to an external processing/display unit, and said cap includes an opening for said connector configured to keep fluids from the environment from reaching the reusable portion around the connector; (g) a clip mounted to said cap and configured to releasably engage said connector to maintain contact between the connector and said contact at the distal end of the reusable portion; (h) more than four fifths of the length of the reusable portion along said handle axis are received in said handle in the assembled endoscope and less than a fifth protrudes from the handle; (i) more than three quarters of the length of the reusable portion along said handle axis are received in said handle in the assembled endoscope and less than a quarter protrudes from the handle; (j) said internal lumen has a constant internal size from said proximal port to said distal port; and (k) a manual switch at the distal end of the reusable portion, wherein at least the portion of the cap that is over the switch is sufficiently flexible for manual operation of the switch through the cap.

According to some embodiments, an endoscope comprises: a single-use portion comprising an elongated housing that extends along a cannula axis, a fluid hub that extends distally from the housing along the cannula axis, and a cannula that extends distally from the fluid hub along the cannula axis and has an imaging module at a distal end, and a handle that extends from the housing along a handle axis that is transverse to the cannula axis and is hollow and has an open distal end: wherein said single-use portion further comprises: a proximal port at a proximal end thereof, an intermediate port at said fluid hub, and a distal port at the distal end of the cannula; an internal lumen in fluid flow communicating with said ports; an electrical contact inside said hollow handle, at a proximal end thereof, that is operatively connected with said imaging module; a cap that is made of a flexible and resilient material and is configured to removably close said open distal end of the handle; and a sterile pouch enclosing said single-use portion, with the cap closing the open end of the hollow handle; wherein said handle is configured for insertion therein of a reusable portion after said cap is removed from the open end of the handle; and said cap is configured to cover the open end of the handle and an adjacent part of the reusable portion after insertion of the reusable portion in the handle to assemble the endoscope.

According to some embodiments, the endoscope described in the immediately preceding paragraph can further include one or more of the following features; (a) a reusable portion configured to be received in said hollow handle after manual removal of said cap from the handle, said reusable portion having a distal part protruding from the handle along said handle axis such that more than half the length of the reusable portion is within said hollow handle; (b) the hollow handle is configured to accept more than two thirds of the length of the reusable portion, so that less than one third of the length of the reusable portion protrudes distally from the handle; (c) the hollow handle is configured to accept more than three quarters of the length of the reusable portion, so that less than one quarter of the length of the reusable portion protrudes distally from the handle; and (d) an external processing/display unit having an image display and connected with the reusable portion wirelessly or by cable to receive and display image data from said imaging module.

According to some embodiments, the endoscope comprises: a single-use portion comprising an elongated housing that extends along a cannula axis, a cannula that extends distally from the housing along the cannula axis and has an imaging module at a distal end, and a hollow, funnel-shaped handle that is integral with the housing, extends from the housing along a handle axis that is transverse to the cannula axis, and has an open distal end; wherein said single-use portion further comprises: a proximal port at a proximal end thereof, a distal port at the distal end of the cannula, and an intermedial port between said proximal and distal ports, and an internal lumen in fluid flow communication with said ports. The endoscope further comprises: a reusable portion configured for manual insertion of a proximal part thereof into the hollow handle through said open distal end of the handle such that a protruding distal portion of the reusable portion protrudes distally from the handle; wherein said proximal part of the reusable portion is more than half the length of the reusable portion along said handle axis; and a cover made of a flexible and resilient material, configured to fit over the open end of the hollow handle before insertion of the reusable portion in the handle and to cover the protruding part of the reusable portion and an adjacent portion of the handle after insertion of the reusable part in the handle.

According to some embodiments, the endoscope described in the immediately preceding paragraph can further include one or more of the following features; (a) the handle is configured to accept more than two thirds of the reusable portion's length such that less than a third of the reusable portion's length protrudes distally from the handle; and (b) the handle is configured to accept more than three quarters of the reusable portion's length such that less than a quarter of the reusable portion's length protrudes distally from the handle.

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all such details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

As described in detail below, an endoscope according to a preferred embodiment is essentially self-contained, communicating with an external display unit wirelessly, for example via WiFi or a near field link, but can also have a port for a cable connection to an external display unit in case a wireless connection is not available or desirable at a medical site. The endoscope can contain a power source as well as sufficient electronics to control an imaging module at the distal end of a cannula and for processing image data from the imaging module into images for display so that only minimal control and/or processing is required at an external display to show the images. In other preferred examples, the external display unit can contain facilities to control some or all the functions of the imaging module and to do some or all the processing of image data from the imaging module for display.

Figure 2:
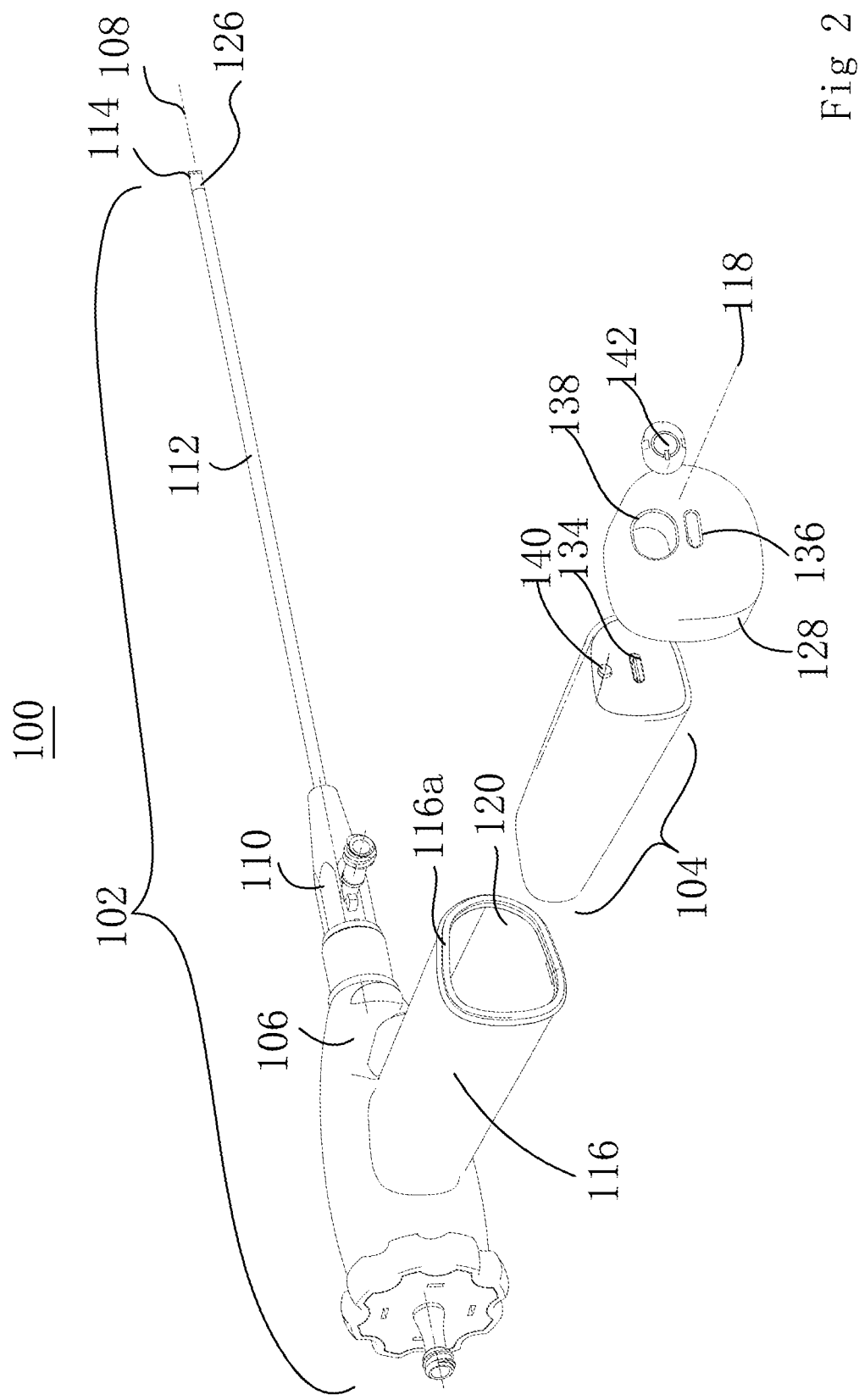
Figure 3A:
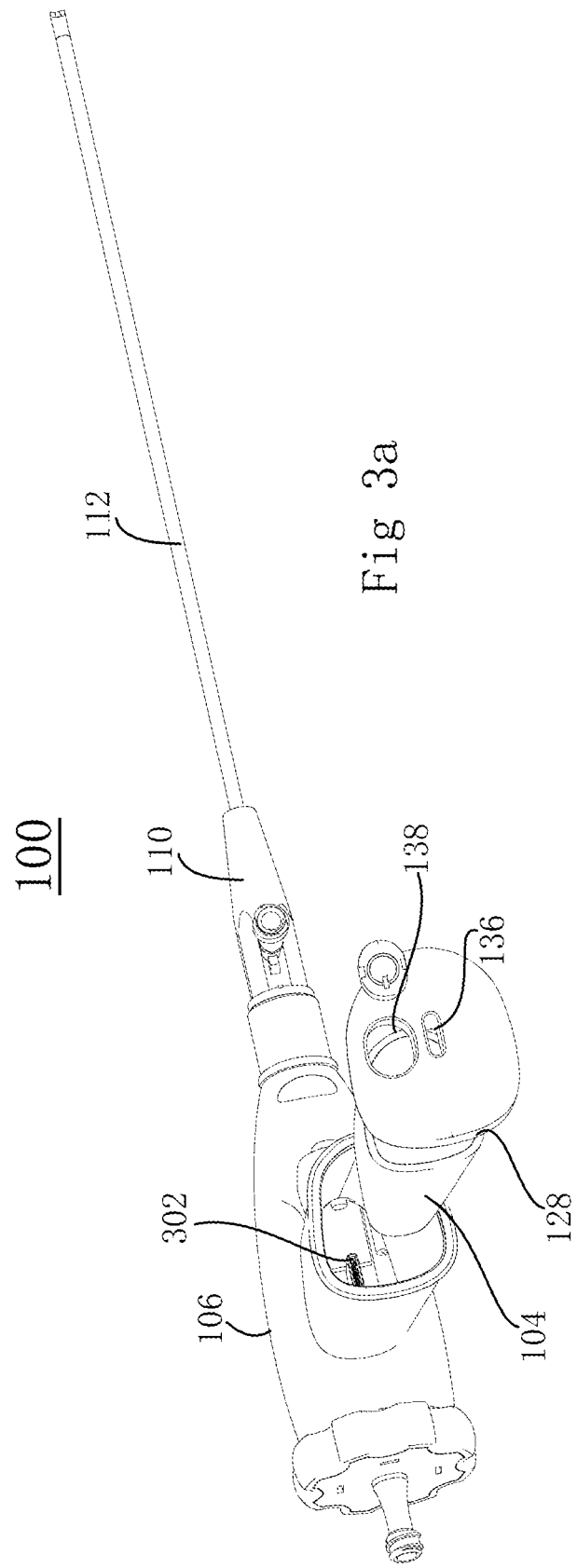

FIG. 1 is a perspective view of an assembled endoscope 100 and FIGS. 2, 3a and 3b are exploded view of an endoscope 100, according to some embodiments. Endoscope 100 comprises a single-use portion 102 and a reusable portion 104 that when assembled form an endoscope. Single-use portion 102 comprises an elongated housing 106 that extends along a cannula axis 108, a fluid hub 110 that extends distally along the cannula axis 108 from housing 106, and a cannula 112 that extends distally from the fluid hub 110 along cannula axis 108 and has an imaging module 114 at its distal end. Single-use portion 102 further comprises a hollow, funnel-shaped, pistol-grip handle 116 that extends from housing 106 along a handle axis 118 that is transverse to cannula axis 108, has a proximal end that is integral with housing 106 and an open distal end 120 (FIG. 2). Single-use portion 102 further comprises an electrical contact 302 (FIG. 3a) inside and at the proximal end of handle 116, an internal lumen 902 (FIG. 9), a proximal port 122 at the proximal end of housing 106, an intermediate port 124 at fluid hub 110, and a distal port 126 at the distal end of cannula 112. Each of ports 122, 124 and 126 is in fluid flow communication with internal lumen 904, which extends along cannula axis 108 all the way from port 122 to port 126 and preferably has a substantially constant cross-section. A cap 128 is made of a flexible and resilient material such as silicone and covers the distal end of handle 116.

According to some preferred embodiments, endoscope 100 wirelessly communicates with an external processing/display unit 1502 (FIG. 15). In other preferred embodiments, endoscope 100 communicates with an external processing/display unit 1400 (FIG. 14) via a cable connection. In some preferred embodiments, endoscope 100 is provided both with an internal battery for controlling imaging module 114 and for processing image date therefrom into images and with a port for a cable connection to an external processing/display unit 1400. FIGS. 1 and 2 illustrate a port with a contact 134 for cable connection to processing/display unit 1400 but is should be understood that this port may be omitted in examples of an endoscope 100 that only communicates wirelessly with an outside unit such as 1502.

Preferably, endoscope 100 is provided with facilities both the wireless and for cable communication with an external processing/display unit. For cable communication, a contact 130 of a cable 132 plugs into a contact 134 (FIG. 2) at the distal end of reusable portion 104 through an opening 136 in cap 128. Another opening 138 accepts an electrical switch 140 protruding distally from the distal end of reusable portion 104, and a smaller cap 142 covers and seals opening 138. Note that FIG. 2 illustrates a variation of the configuration of FIG. 1—in FIG. 1 electrical contact 134 and switch 140 are spaced from each other in the direction of cannula axis 108 while in FIG. 2 they and their respective openings 138 and 166 are spaced in a direction perpendicular to axis 108 and are closer to each other. Still in addition, single-use portion 102 includes a thumb wheel 144 that is coupled with cannula 112 through fluid hub 110 such that manual rotation of thumb wheel 142 about cannula axis 108 rotates cannula 112 (and preferably hub 110 as well) around cannula axis 108. Preferably, a clip 148 is anchored on cap 128 and swings to keep connector 130 in place. In examples where only wireless communication is desirable, contact 130 and cable 132 and its plug 130, as well as clip 148, can be omitted, and the distal wall of cap 128 need not have an opening such as 136.

Referring to FIG. 2, reusable portion 104 is elongated along axis 118 and is configured for insertion in handle 116. At a proximal end, reusable portion 104 has an electrical contact 146 (FIG. 3b) that mates with electrical contact 302 (FIG. 3a) in handle 116 when reusable portion 104 is inserted all the way into handle 116. Internal cables (not shown) connect imaging module 114 with cable 132 through contacts 302, 146 and 134 and connector 130 for transfer of power and image data. As noted, contact 134 can be omitted in examples that do not need cable communication to an outside processing/display unit.

Notably, to ensure ease of assembling endoscope 100 and correctly fitting reusable portion 104 into handle 116, the handle and the reusable portion are shaped such that the reusable portion can be inserted in the handle in only one orientation. For example, as seen in FIG. 2, the left side of open end 120 of handle 116 is less curved that the right side and the proximal end of reusable portion 104 is similarly shaped to ensure that the insertion orientation is correct and will result in mating electrical contacts 302 and 146. Note that the distal part of reusable portion 104 is larger, so that reusable portion 104 cannot be inserted backward into handle 116.

FIGS. 3a and 3b are exploded views of endoscope 100 from different viewpoints. A noted above, the orientation and spacing of elements such as openings 136 (and switch 140) and 138 (and contact 134) are variations of those in FIG. 1. Like-numbered component are the same or similar and serve the same or similar functions in FIGS. 1-3b as in all other figures.

Figure 4:
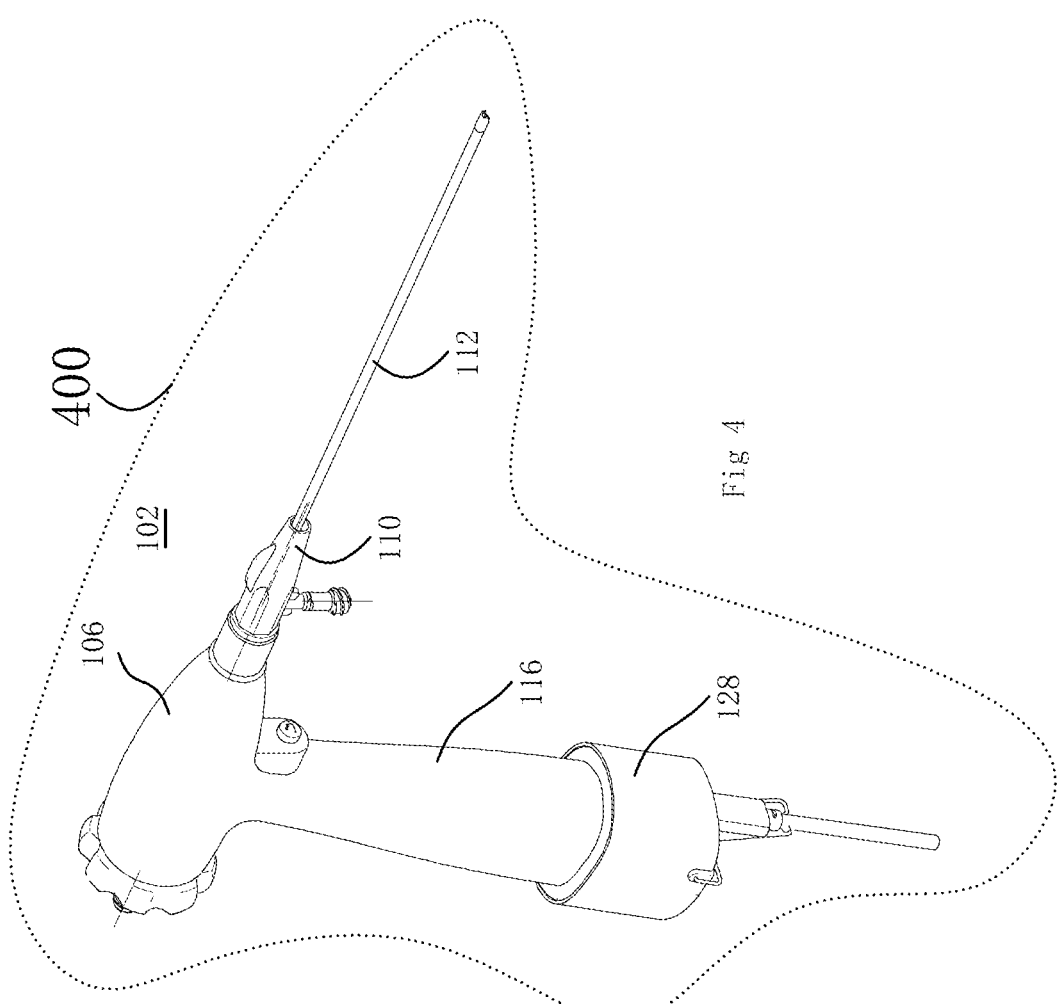
FIG. 4 is a perspective view of a single use portion of an endoscope, with the open end of a handle thereof covered with a removable cap, in a sterile pouch, according to some embodiments.

FIG. 4 is a perspective view of single-use portion 102, with cap 128 removably secured to and covering the open end of handle 116, in a sterile pouch 400, according to some embodiments. Preferably, single-use portion 102 and cap 128 are packaged in this manner at the manufacturing site and kept in this form until needed for a medical procedure. For a medical procedure, sterile pouch 400 is torn and discarded, cap 128 is removed manually from handle 116, reusable portion 104 is inserted in handle 116, and cap 128 that was removed from handle 116 is now placed over the distal end of reusable portion 104 and an adjacent part of handle 116. In the example of providing for a cable connection to an outside processing/display unit, connector 130 plugs in to mate with contact 134 to thereby connect the so-assembled endoscope 100 to an external display and/or image processing unit described further below. Also described further below are details about how cap 128 is kept in place and how it seals reusable portion 104 and the interior of handle 116.

Figure 5:
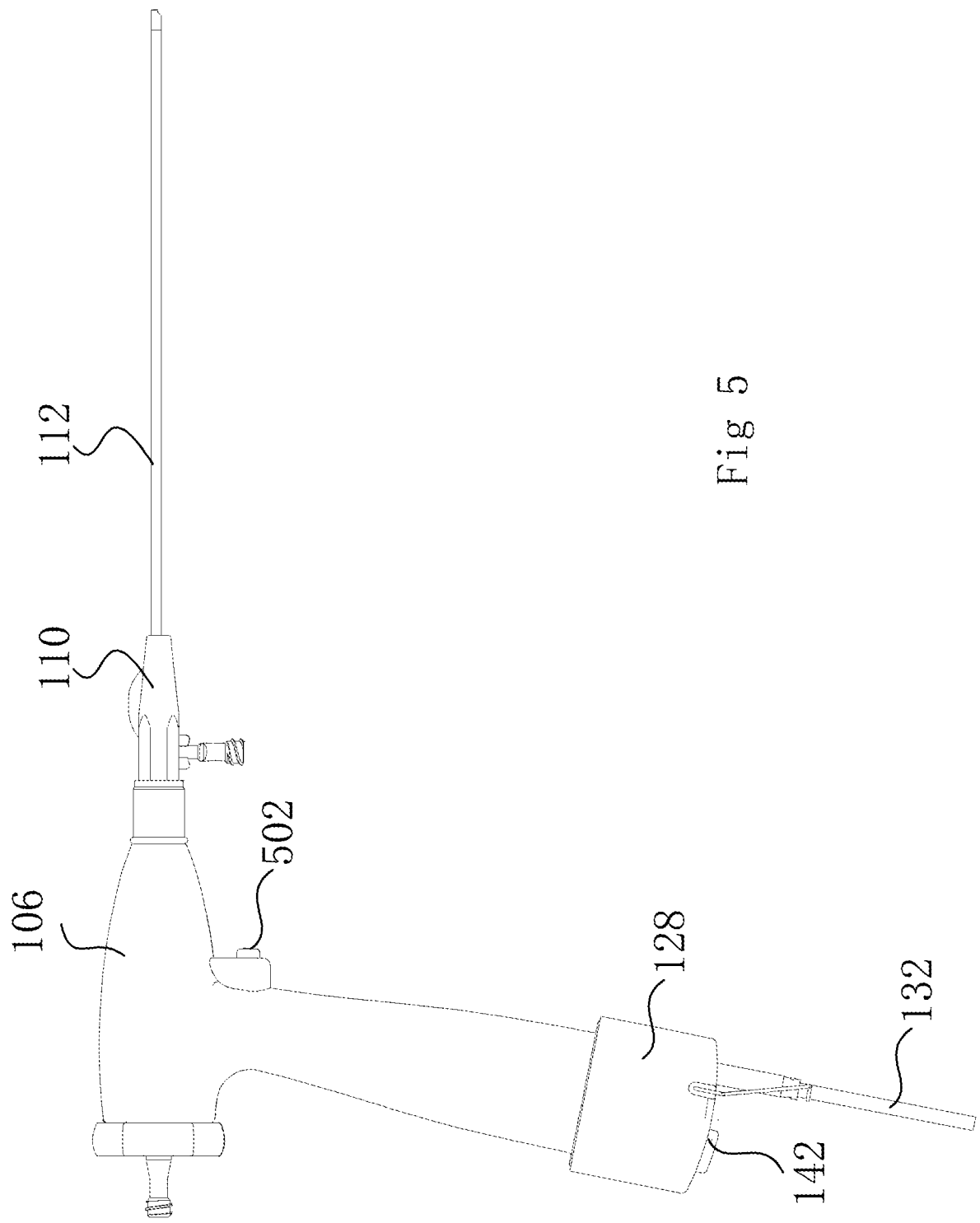
FIGS. 5, 6, 7, and 8 are, respectively, a side view, a back elevation, a top view, and a front elevation of an endoscope, according to some embodiments.
Figure 6:
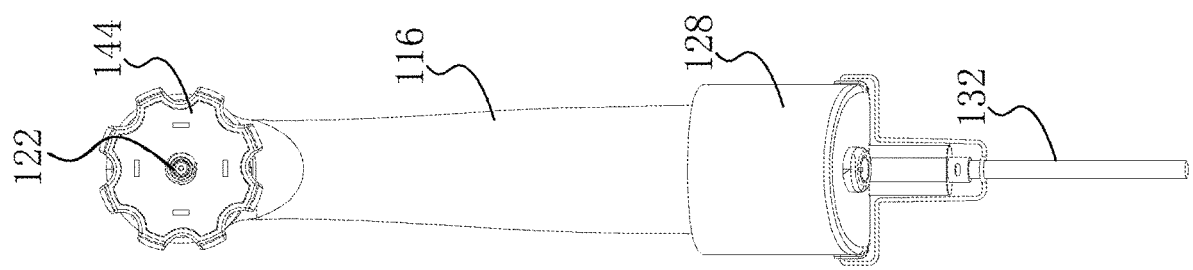
Figure 7:
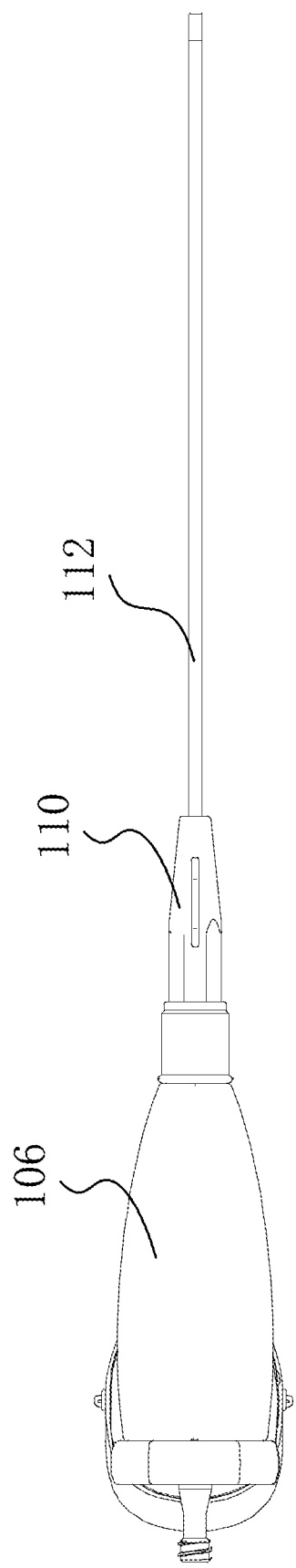
Figure 8:
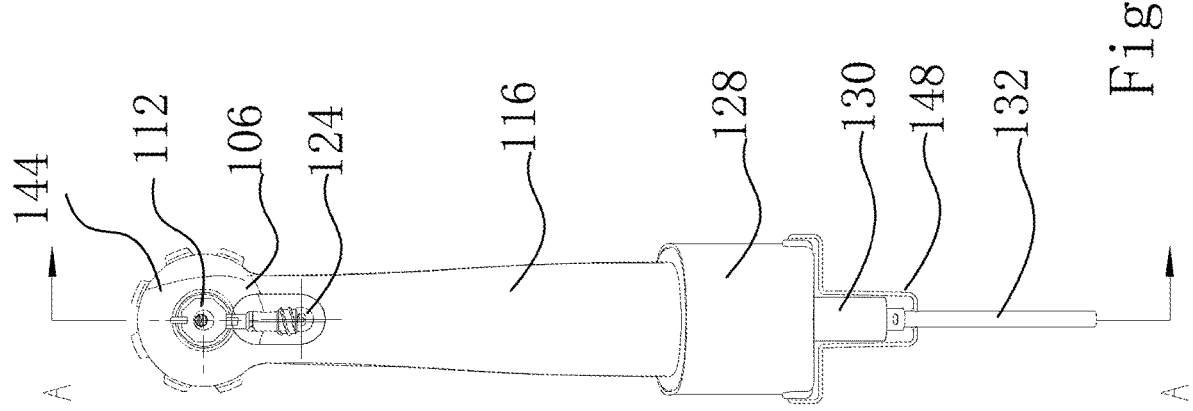

FIGS. 5-8 are, respectively, a side elevation, a back elevation, a top view, and a front elevation of endoscope 100, according to some embodiments. FIG. 5 illustrates a switch 502 that is positioned for operation by a user's forefinger and can serve a function such as taking a photo or a video clip with imaging module 114 or some other function. The switch at 142 can be used for the same or different function, such as powering imaging module 114. In other respects, FIGS. 5-8 illustrate the same endoscope 100, accounting for the variations in orientation and spacing of components at the distal end of reusable portion 104 and cap 128 described above.

Figure 9:
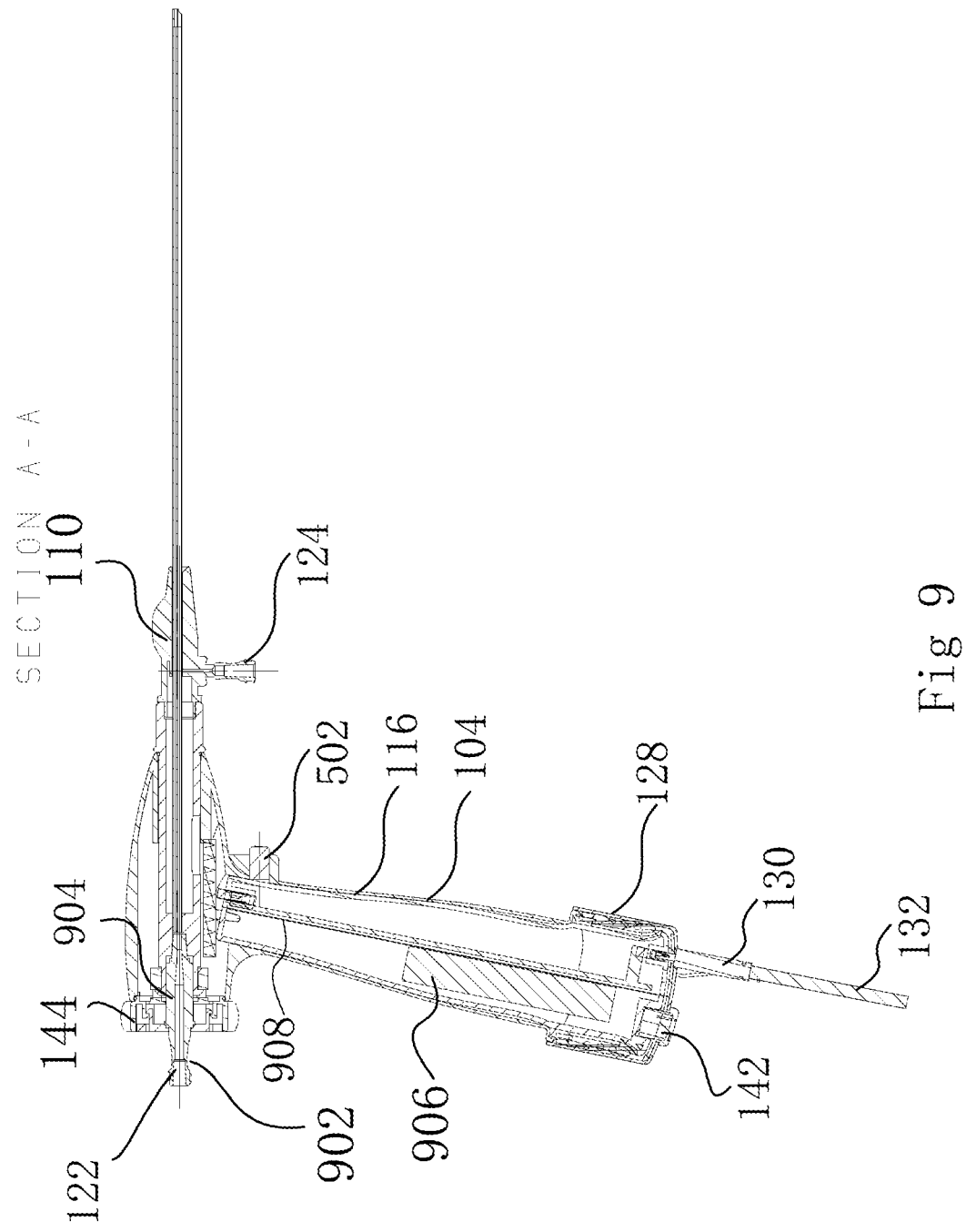
FIG. 9 is a sectional view of an endoscope, according to some embodiments.

FIG. 9 shows an important feature of endoscope 100—nearly the entire length of reusable portion 104 is inside handle 116, according to some embodiments. For example, more than 9/10, or 4/5, or 3/4, or 1/2 of the length of reusable portion along axis 118 is received in handle 116. The minor part of the length of reusable portion 104 that protrudes distally from handle 116 is covered with cap 128, and the cap also covers an adjacent portion of handle 116. In this configuration, cap 128 an hollow handle 116 protect the entire reusable portion 104 from contamination in a medical procedure. After the medical procedure, cap 128 is removed by hand, reusable portion 104 pulls out of handle 116, single-use portion 102 is discarded as medical waste, and reusable portion 104 only needs moderate cleaning or disinfection before being assembled in a new endoscope 100 with another, new single-use portion 102.

Still referring to FIG. 9, a proximal portion of lumen 902 can have a duck bill valve 904 at its distal end, which valve is normally closed to prevent backflow of fluid out of proximal port 122. However, the leading end of a surgical implement (not shown) introduced distally through proximal port 122 spreads valve 904 so the surgical instrument can move distally through valve 904 and then through the rest of lumen 904 all the way through housing 106, hub 110, and cannula 112 and to exit through distal port 126. Preferably, intermediate port 124 communicates with the same lumen 902 such that fluid injected into port 124 can be expelled through distal port 126 or suction applied to port 124 can extract fluid entering through distal port 126. If no fluid flow through port 124 is desired, the port can be closed with a cap (not shown).

Reusable portion 104 can include a rechargeable battery 906 operatively coupled to power imaging module 114 through one of switches 140 and/or 502 and internal cables (not shown) in reusable portion 104 and single-use portion 102. In addition, reusable portion 104 can include electronics 908 communicating with imaging module 114 to control the imaging module and to process image data from the imaging module. According to some embodiments, electronics 908 can include a WiFi or near-filed facility to communicate with an external processing/display unit such as 1502, and facilities to fully or nearly fully control the operation of imaging module 114 through suitable switches and to fully or nearly fully process the image data from module 114 into images for display, so that an outside processing/display unit such as unit 1400 or 1502 needs to do only minimal processing of image data or of display images. According to some embodiments, some or all of the control over imaging module 114 and some or all the processing of image data from module 114 can be done at an external processing/display unit such as 1400 or 1502.

Figure 10:
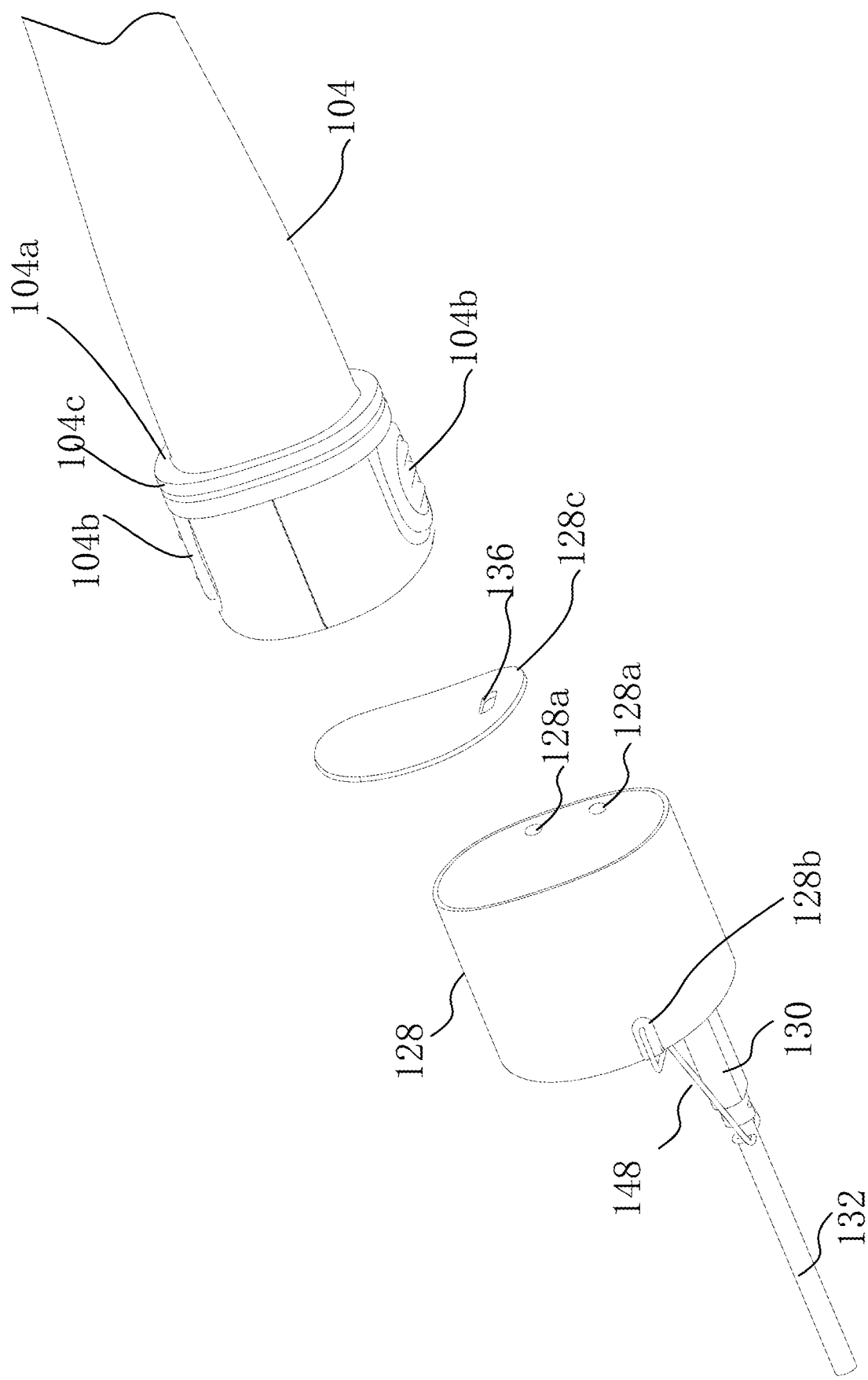
FIGS. 10 and 11 are exploded perspective views, taken from different viewpoints, of portions of an endoscope, according to some embodiments.
Figure 11:
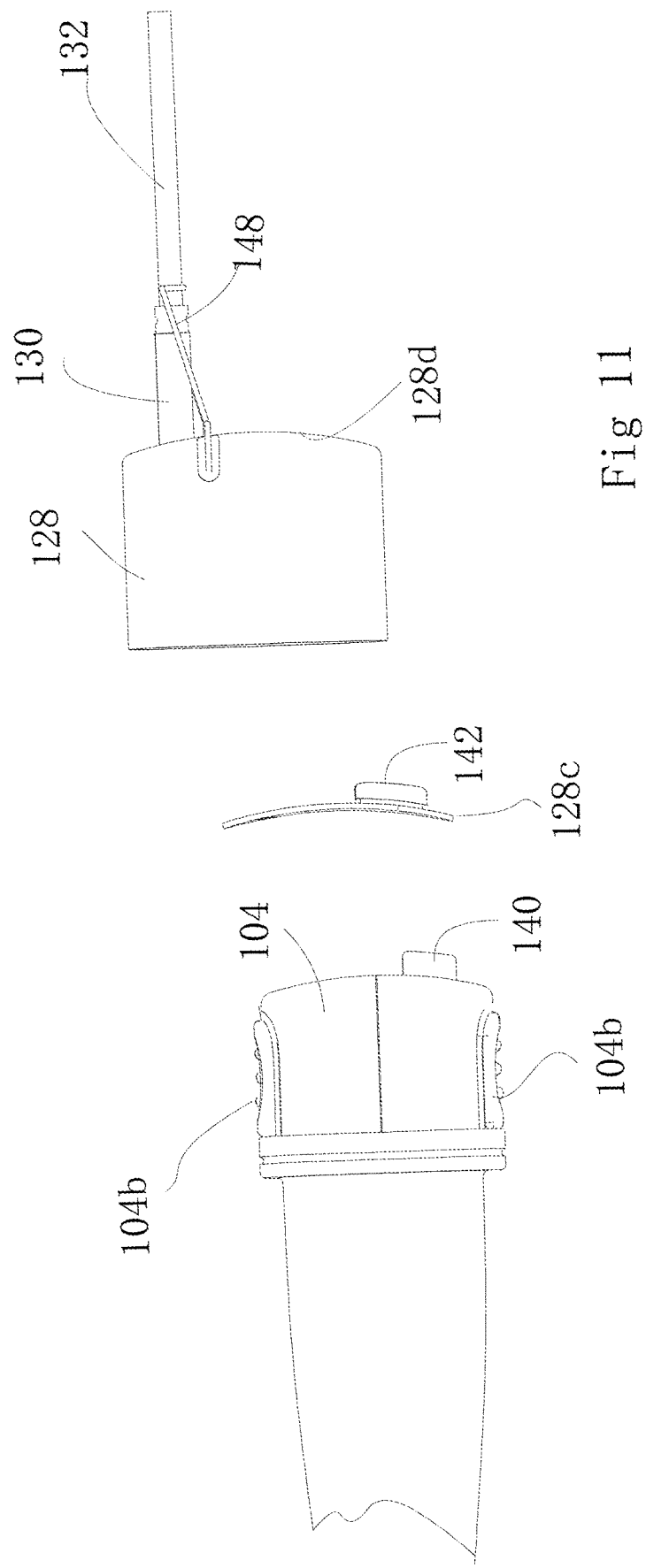

FIGS. 10 and 11 are exploded perspective view showing details of cap 128 and the distal portion of reusable portion 104 from two viewpoints, according to some embodiments. Referring to FIG. 10, the distal end of reusable portion 104 is larger than the remainder of portion 104 and ends at a ledge 104a so that when portion 104 is fully inserted in housing 116 this ledge 104a is flush with the opening 120 (FIG. 2) in hollow handle 116. The distal part of reusable portion 104 can have ribbed portions 104b to help a user grasp and hold portion 104 when inserting in handle 116 or withdrawing from handle 116. Cap 128 preferably has at its internal surface bumps 128a configured to be positioning distally of a rib 116a (FIG. 2) that surrounds and extends radially outwardly from opening 120 in handle 116 when endoscope 100 is assembled as seen in FIG. 1, to thereby help keep cap 128 in place.

Importantly, when endoscope 100 is assembled, cap 128 covers not only the part of reusable portion 104 that protrudes distally from handle 116 but also an adjacent part of handle 116 to thereby seal the interface between the open end of handle 116 and reusable portion 104. Additional bumps can be provided on the inside of cap 128 to engage a channel 104c in the protruding distal part of reusable portion 104, to help keep cap 128 in place in the assembled endoscope 100.

FIG. 10 also shows the sheet 128c made of a soft and pliable material that sits at the inside of a distal wall 128d (FIG. 11) of cap 128 and helps seal the distal end of reusable portion 104 and especially switch 140 and the interface between contact 134 and connector 130 from the environment. Sheet 128c has an opening 136 for connector 130. Cap 128 has two indentations 128b, of which only one is visible, to anchor clip 148 such that the clip can pivot about those indentations to lock connector 130 in place of to release it so connector 130 can pull from endoscope 100 and the endoscope can be disassembled by pulling out cap 128 and then pulling out reusable portion 104 from single-use portion 102. FIG. 11 illustrates the same components as FIG. 10 but from a different viewpoint. In FIG. 11, switch 140 is visible, and sheet 128c in this case shows the smaller cap 142 that covers the opening 138 (FIG. 3) through which switch 140 can extend when endoscope 100 is assembled. The arrow in FIG. 11 shows where wall 128d is in cap 128.

Figure 12:
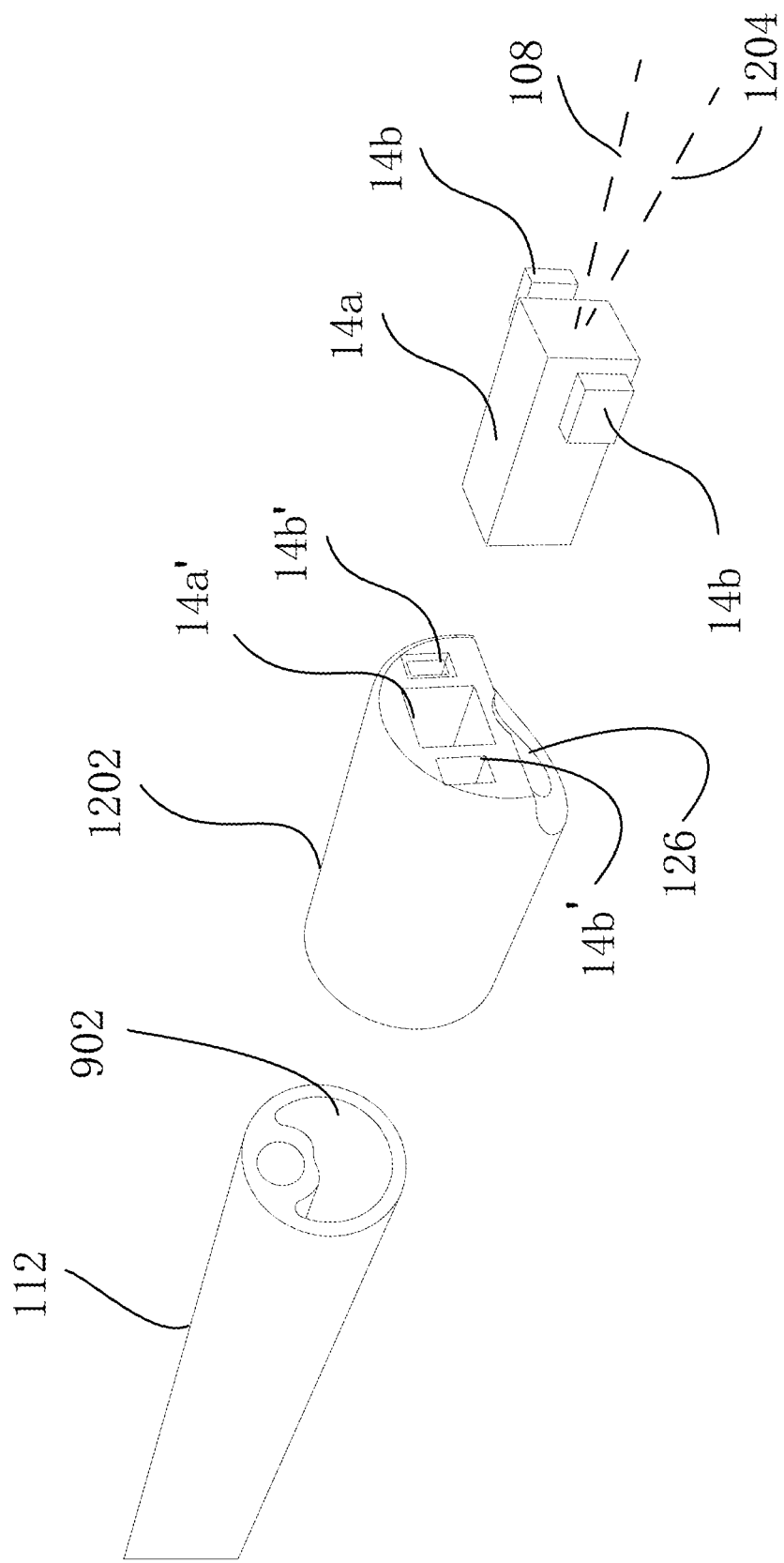
FIG. 12 is an exploded perspective view of a distal part of a cannula of an endoscope, according to some embodiments.

FIG. 12 is an exploded perspective view of a distal portion of cannula 112, according to some embodiments. Video camera 14a and LED lights 114b fit in respective openings 14a' and 14b' in a housing 1202 secured at the distal end of cannula 112 such that the camera and LEDs face in the distal direction. Camera1 14a and LEDs 14b can be configured to have a field of view and a direction of illumination having a central axis 1204 that is at an angle to cannula axis 108, for example a 30 degrees angle.

Figure 13:
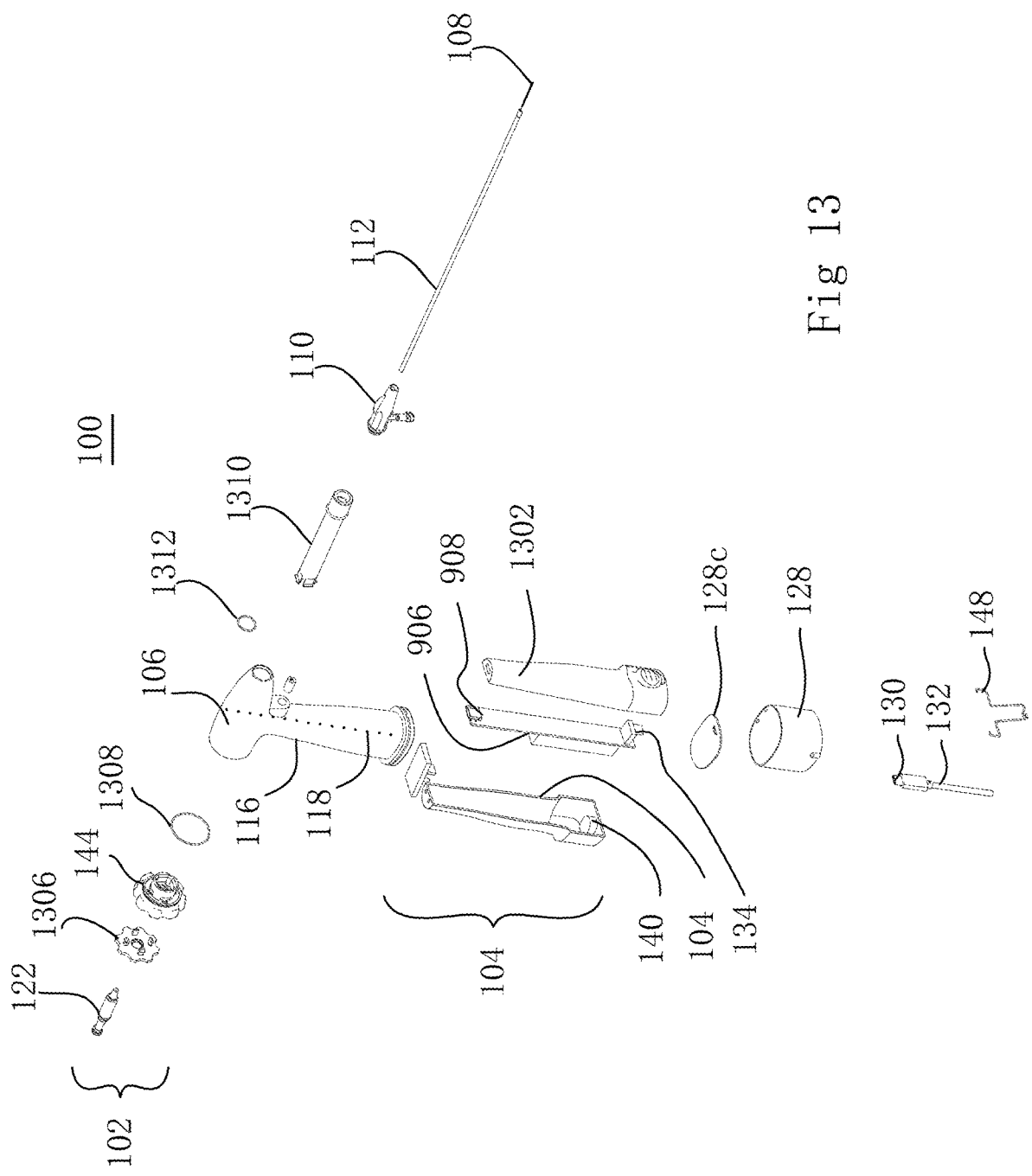
FIG. 13 is an exploded perspective view of components of an endoscope, according to some embodiments.

FIG. 13 is an exploded perspective view of components of single-use portion 102 and reusable portion 104, according to some embodiments. Many of the components are designated by reference numerals discussed above. The component of single-use portion 102 seen only in FIG. 13 include a cap 1306 for thumbwheel 144, an O-ring 1308 to seal thumbwheel 144 against housing 106, a bridge tube 1310 connecting proximal port 122 and thumbwheel 144 to fluid hub 110 and a seal 1312 sealing tube 1310 to housing 106. The component of reusable portion 104 that are seen only in FIG. 13 are two half shells 1302 and 1304 that form handle when affixed to each other. As noted, components related to a cable connection with an external unit can be omitted in examples where only a wireless connection is desired.

Figure 14:
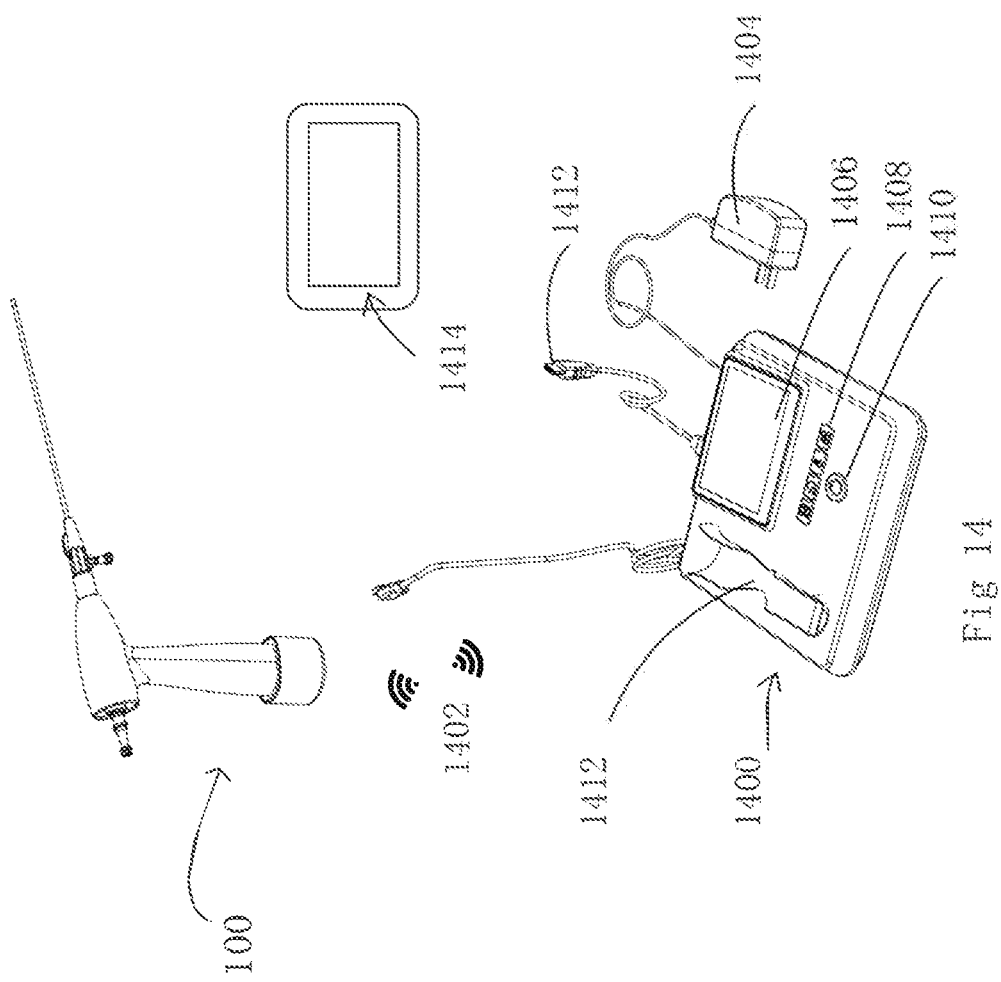
FIG. 14 is a perspective view of a remote station suitable for operation with an endoscope, according to some embodiments.

FIG. 14 is a perspective view of an endoscope 100 and an external processing/display unit or station 1400 that connects with endoscope 100 through a wireless link 1402 and/or through cable 132 and contact 130 in the example where a cable connection is used. Unit 1400 is powered through a plug 1404 from an electrical outlet. Unit or station 1400 comprises a display 1406 configured to display images from camera 114 at the distal end of cannula 112 and/or other data and images, a row of switches 1408 configured to control functions of endoscope 100 and station 1400, and an on-off switch 14108. In addition, station 1400 has a cradle 1412 for reusable portion 104 that may include provisions (not shown) for charging battery 906 in reusable portion 104. In addition. Unit 1400 can include a cable and an HDMI 1412 or another high-speed connector for a data link to an external display 1414 that can be a large and/or high-definition monitor or a workstation. Wireless link 1402 also can be used for a connection of endoscope 100 and/or unit 1400 with another device such as a smartphone or a tablet or a workstation. The wireless link can be WiFi link or can use a near filed communication protocol (NFC) or another protocol.

According to some embodiments, wireless link 1402 is configured such that transmission between endoscope 100 and unit 1400 is automatically established. Unit 1400 is configured such that after being turned ON, it searches for an finds a wireless endoscope 100 that is within range and has been turned ON, for example by switch 140, Unit 1400 then automatically connects to this endoscope 100 for receiving and transmitting wireless data. This transmission can comprise image and/or other data from endoscope 100 and/or transmission of commands and/or other information from unit 1400.

Preferably, according to some embodiments the wireless transmission between endoscope 100 and unit 1400 uses a proprietary protocol and/or encoding designed to keep the transmitted information private, thus preserving confidentiality of medical information. This can limit or prevent access of public wireless receivers or transmitters to confidential information and possible corruption of the transmitted information by other actors.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

The invention claimed is:

1. An endoscope comprising:
a single-use portion comprising:
an elongated housing extending along a cannula axis;
a fluid hub extending distally along the cannula axis from the housing;
a cannula that extends distally from the fluid hub along the cannula axis and has an imaging module at a distal end;
a hollow, funnel-shaped, pistol-grip handle that extends from the housing along a handle axis that is transverse to the cannula axis, has a proximal end that is integral with the housing and an open distal end;
an electrical contact inside and at the proximal end of the handle, operatively coupled with said imaging module;
a proximal port at a proximal end of the housing, an intermediate port at the fluid hub, and a distal port at a distal end of the cannula;
an internal lumen from the proximal port to the distal port, in fluid flow communication with said proximal, intermediate and distal ports;
wherein said fluid hub and cannula are mounted for rotation about the cannula axis relative to the housing; and
a manual rotation control at the proximal end of the housing coupled with the fluid hub to rotate the fluid hub and cannula relative to the housing about the cannula axis;
an elongated reusable portion having a proximal part configured for insertion in the handle along the handle axis and having an electrical contact at a proximal end configured to mate with the electrical contact in the handle when the proximal part of the reusable portion is inserted in the handle; and
a cap made of a flexible and resilient material, configured to cover the open distal end of the handle before the reusable portion is inserted in the handle, to be manually removed from the handle prior to insertion of the reusable portion in the handle, and after insertion of the reusable portion in the handle to cover a distal part of the reusable portion that protrudes from the handle along the handle axis as well as an adjacent part of the handle to thereby cover said protruding part of the reusable portion and an interface between the open distal end of the handle and the reusable portion.

2. The endoscope of claim 1, further comprising a sterile pouch enclosing said single use portion, with the cap over and covering the open distal end of the handle, before assembly of the single-use and reusable portions into said endoscope.

3. The endoscope of claim 1, in which said reusable portion includes a battery and control and processing electronics configured to control said imaging module to take images in a field of view and to receive image data from the imaging module, and further includes a facility to convey image data from the endoscope to an external processing/display unit.

4. The endoscope of claim 1, in which said facility is configured to convey image data by wireless transmission.

5. The endoscope of claim 3, in which said facility in the reusable portion is configured to convert received image data into display images and convey display images to an external unit for display.

6. The endoscope of claim 3, in which said facility comprises a wireless transmitter/receiver in said reusable portion and further including an external processing/display unit having a wireless transmitter/receiver configured to communicate wirelessly with said transmitter/receiver in the reusable portion and to receive wirelessly and process into display images image data received from the reusable portion, and a display configured to display said display images.

7. The endoscope of claim 6, in which said external processing/display unit is configured to automatically search for and connect wirelessly with said reusable portion upon turning ON when the reusable portion is ON and in range.

8. The endoscope of claim 3, in which said facility comprises an electrical contact at the distal end of the reusable portion configured to mate with a connector of a cable to an external processing/display unit, and said cap includes an opening for said connector configured to keep fluids from the environment from reaching the reusable portion around the connector.

9. The endoscope of claim 8, further including a clip mounted to said cap and configured to releasably engage said connector to maintain contact between the connector and said contact at the distal end of the reusable portion.

10. The endoscope of claim 1, in which more than four fifths of the length of the reusable portion along said handle axis are received in said handle in the assembled endoscope and less than a fifth protrudes from the handle.

11. The endoscope of claim 1, in which more than three quarters of the length of the reusable portion along said handle axis are received in said handle in the assembled endoscope and less than a quarter protrudes from the handle.

12. The endoscope of claim 1, in which said internal lumen has a constant internal size from said proximal port to said distal port.

13. The endoscope of claim 1, further comprising a manual switch at the distal end of the reusable portion, wherein at least the portion of the cap that is over the switch is sufficiently flexible for manual operation of the switch through the cap.

* * * * *